United States Patent
Barth et al.

(10) Patent No.: US 7,282,516 B2
(45) Date of Patent: Oct. 16, 2007

(54) 4-CYANOPYRAZOLE-3-CARBOXAMIDE DERIVATIVES, PREPARATION, AND APPLICATION THEREOF

(75) Inventors: Francis Barth, Montpellier (FR); Christian Congy, Saint Gely du Fesc (FR); Serge Martinez, Montpellier (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/315,774

(22) Filed: Dec. 22, 2005

(65) Prior Publication Data

US 2006/0135776 A1 Jun. 22, 2006

Related U.S. Application Data

(63) Continuation of application No. PCT/FR2004/001580, filed on Jun. 24, 2004.

(30) Foreign Application Priority Data

Jun. 25, 2003 (FR) .................... 03 07698

(51) Int. Cl.
*A61K 31/4155* (2006.01)
*A61K 31/454* (2006.01)
*C07D 231/16* (2006.01)

(52) U.S. Cl. ................ 514/406; 548/364.1; 548/377.1; 548/357.1; 514/359

(58) Field of Classification Search ........... 514/406, 514/326; 548/374.1, 377.1, 357.5, 361.1, 548/364.1

See application file for complete search history.

(56) References Cited

U.S. PATENT DOCUMENTS 6,028,084 A 2/2000 Barth et al.

6,344,474 B1 2/2002 Maruani et al.

OTHER PUBLICATIONS

Meschler et al. Biochemical Pharmacology, (2000), 60, p. 1315-23.*
Ahmad Sami Shawali, Synthesis and Tautomeric Structure of some 2H-Pyrazolo [3,4-d] pyridazines, J. Heterocyclic Chem. (1977, pp. 375-381, vol. 14, No. 3).
Justin P. Meschler et al., Inverse Agonist Properties of -(Piperidin-1-yl)-5-(4-chlorophenyl) -1-(2,4-dichlorophenyl)-4-methyl-1H-pyrazole-3-carboxamide HCI (SR141716A) and -(2-Chlorophenyl) -4-cyano-5-(4-methoxyphenyl)-1H-pyrazole-3-carboxylic Acid Phenylamide (CP-272871) for the CB1 Cannabinoid Receptor, Biochemical Pharmacology (2000, pp. 1315-1323, vol. 60, No. 9).
1H-Pyrazole-3-carboxylic acid, 1-(4-bromophenyl)-4-cyano-5-(4-methoxyphenyl)-, ethyl ester, Chemical Abstract 2003:1939325, (Jul. 9, 2002).

* cited by examiner

*Primary Examiner*—Rebecca Anderson
*Assistant Examiner*—Yong Chu
(74) *Attorney, Agent, or Firm*—Balaram Gupta

(57) ABSTRACT

The invention relates to 4-cyanopyrazole-3-carboxamide derivatives of formula (I):

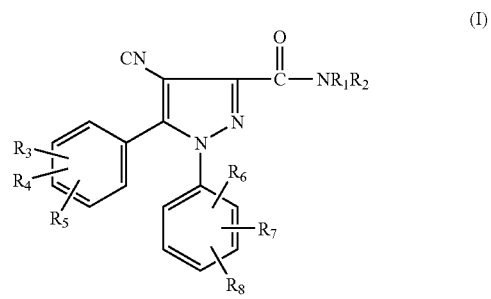

in which $R_1$, $R_2$, $R_3$, $R_4$, $R_5$, $R_6$, $R_7$, $R_8$ are as described herein. Also disclosed and claimed are the method of preparation and therapeutic application of compound of formula (I).

9 Claims, No Drawings

4-CYANOPYRAZOLE-3-CARBOXAMIDE DERIVATIVES, PREPARATION, AND APPLICATION THEREOF

CROSS REFERENCE TO RELATED APPLICATIONS

This application is a continuation of International application No. PCT/FR2004/001,580, filed Jun. 24, 2004, which is incorporated herein by reference in its entirety; which claims the benefit of priority of French Patent Application No. 03/07,698, filed Jun. 25, 2003.

BACKGROUND OF THE INVENTION

1. Field of the Invention

The present invention relates to 4-cyano-pyrazole-3-carboxamide derivatives, their preparation and their therapeutic application.

2. Description of the Art

A 4-cyanopyrazole-3-carboxamide derivative is known: N-phenyl-1-(2-chlorophenyl)-4-cyano-5-(4-methoxyphenyl)-1H-pyrazole-3-carboxamide which is described in Biochem. Pharmacol., 2000, 60(9), 1315-1323. It is presented as having antagonist properties for the $CB_1$ cannabinoid receptors and more precisely inverse agonist properties for said receptors.

SUMMARY OF THE INVENTION

The subject of the present invention is a compound corresponding to formula (I):

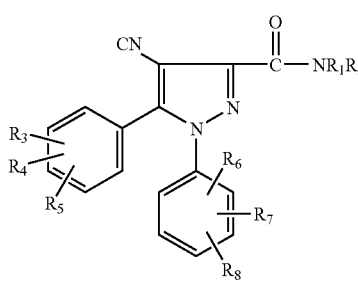

in which:
$R_1$ represents hydrogen or a $(C_1-C_4)$alkyl;
$R_2$ represents:
  a $(C_3-C_7)$alkyl group;
  a nonaromatic $C_3-C_{10}$ carboxyl radical which is unsubstituted or substituted once or several times with a $(C_1-C_4)$alkyl and/or hydroxyl group;
  a phenyl which is substituted once or several times with a halogen atom and/or with a $(C_1-C_4)$alkyl and/or trifluoromethyl and/or $(C_1-C_4)$alkoxy group;
  an $NR_9R_{10}$ group;
  a CH[$(C_1-C_4)$alkyl]benzhydryl group in which one or both of the phenyl groups are unsubstituted or substituted once or several times with a halogen atom and/or with a $(C_1-C_4)$alkyl and/or $(C_1-C_4)$alkoxy group;
or $R_1$ and $R_2$ together with the nitrogen atom to which they are attached constitute a piperidin-1-yl radical which is disubstituted at the 4-position with a phenyl or benzyl group and with a $(C_1-C_4)$alkyl group or a $(C_1-C_3)$alkanoyl;
$R_3, R_4, R_5, R_6, R_7, R_8$ represent, each independently of the other, a hydrogen or halogen atom, a $(C_1-C_6)$alkyl, $(C_1-C_6)$alkoxy or trifluoromethyl group; provided that at least one of the substituents $R_3, R_4, R_5, R_6, R_7, R_8$ is different from hydrogen;
$R_9$ represents a hydrogen atom;
$R_{10}$ represents a $(C_3-C_6)$alkyl;
or $R_9$ and $R_{10}$ together with the nitrogen atom to which they are attached constitute a saturated or unsaturated heterocyclic radical of 5 to 10 atoms, possibly containing a second heteroatom chosen from O or N, said radical being unsubstituted or substituted once or several times with a $(C_1-C_4)$alkyl and/or hydroxyl and/or $(C_1-C_4)$alkoxy and/or methoxy$(C_1-C_2)$alkylene and/or $(C_1-C_4)$alkanoyl group, or substituted with a spirocyclobutane, a spirocyclopentane or a spirocyclohexane;
and their salts, their solvates and their hydrates.

DETAILED DESCRIPTION OF THE INVENTION

The compounds of formula (I) may contain one or more asymmetric carbon atoms. They can therefore exist in the form of enantiomers or diastereoisomers. These enantiomers, diastereoisomers and mixtures thereof, including racemic mixtures, form part of the invention.

The compounds of formula (I) can exist in the salt form. Such addition salts form part of the invention.

These salts are advantageously prepared with pharmaceutically acceptable acids, but the salts of other acids which are useful, for example, for the purification or isolation of the compounds of formula (I) also form part of the invention.

The compounds of formula (I) can also exist in the form of hydrates or solvates, namely in the form of associations or combinations with one or more water molecules or with a solvent. Such hydrates and solvates also form part of the invention.

According to the present invention, it is possible to distinguish the compounds of formula (I) in which:
$R_1$ represents hydrogen or a $(C_1-C_4)$alkyl;
$R_2$ represents:
  a $(C_3-C_7)$alkyl group;
  a nonaromatic $C_3-C_{10}$ carboxyl radical which is unsubstituted or substituted once or several times with a $(C_1-C_4)$alkyl;
  a phenyl which is substituted with a halogen atom and/or with a $(C_1-C_4)$alkyl, trifluoromethyl or $(C_1-C_4)$alkoxy group;
  an $NR_9R_{10}$ group;
  a CH[$(C_1-C_4)$alkyl]benzhydryl group in which one or both of the phenyl groups are unsubstituted or substituted with a halogen atom or with a $(C_1-C_4)$alkyl or $(C_1-C_4)$alkoxy group;
or $R_1$ and $R_2$ together with the nitrogen atom to which they are attached constitute a piperidin-1-yl radical which is disubstituted at the 4-position with a phenyl or benzyl group and with a $(C_1-C_4)$alkyl group or a $(C_1-C_3)$alkanoyl;
$R_3, R_4, R_5, R_6, R_7, R_8$ represent, each independently of the other, a hydrogen or halogen atom, a $(C_1-C_6)$-alkyl, $(C_1-C_6)$alkoxy or trifluoromethyl group;
provided that at least one of the substituents $R_3, R_4, R_5, R_6, R_7, R_8$ is different from hydrogen;
$R_9$ represents a hydrogen atom;

$R_{10}$ represents a $(C_3-C_6)$alkyl;

or $R_9$ and $R_{10}$ together with the nitrogen atom to which they are attached constitute a saturated or unsaturated heterocyclic radical of 5 to 10 atoms, possibly containing a second heteroatom chosen from O or N, said radical being unsubstituted or substituted once or several times with a $(C_1-C_4)$alkyl, hydroxyl or $(C_1-C_4)$ alkoxy group, methoxy$(C_1-C_2)$alkylene, or substituted with a spirocyclobutane, a spirocyclopentane or a spirocyclohexane; and their salts, their solvates and their hydrates.

In the context of the present invention, the expression:

alkyl group is understood to mean a linear or branched radical such as methyl, ethyl, propyl, isopropyl, butyl, isobutyl, tert-butyl, n-pentyl, isopentyl, n-hexyl, isohexyl, the methyl group being preferred for a $(C_1-C_4)$ alkyl; the tert-butyl groups, 1,1-dimethylpropyl and 2-methylbutyl-2 being preferred for a $(C_3-C_7)$alkyl;

$(C_1-C_4)$alkoxy group is understood to mean a linear or branched radical containing 1 to 4 carbon atoms, the methoxy group being preferred;

halogen atom is understood to mean a fluorine, chlorine, bromine or iodine atom, the fluorine, chlorine or bromine atoms being preferred.

The $C_3-C_{10}$ carbocyclic or aromatic radicals comprise fused or bridged mono- or polycyclic radicals. The monocyclic radicals include cycloalkyls, for example cyclopropyl, cyclobutyl, cyclopentyl, cyclohexyl, cycloheptyl, cyclooctyl; cyclohexyl and cyclopentyl being preferred. The fused, bridged or spiro di- or tricyclic radicals include for example the bicyclo[2.2.1] heptanyl, bicyclo[3.1.1]heptanyl, bicyclo[2.2.2. ]octanyl, bicyclo[3.2.1]octanyl, bicyclo-[3.2.1]octanyl, and adamantyl, bicyclo[3.1.1]heptanyl and bicyclo[3.2.1] octanyl being preferred.

The expression saturated or unsaturated heterocyclic radical of 5 to 10 atoms, containing or otherwise a second heteroatom such as O or N is understood to mean radicals such as morpholin-4-yl, piperidin-1-yl, piperazin-1-yl, pyrrolidin-1-yl, 3,6-dihydropyridin-1-yl, and octahydrocyclopenta[c]-pyrrol-2-yl, the piperidin-1-yl and morpholin-4-yl radicals being preferred.

According to the present invention, the compounds of formula (I) are preferred in which:

$R_1$ represents a hydrogen atom or a $(C_1-C_4)$alkyl group, preferably a hydrogen atom;

$R_2$ represents a $(C_3-C_7)$alkyl group or an $NR_9R_{10}$ group in which $R_9$ and $R_{10}$ together with the nitrogen atom to which they are attached constitute a piperidin-1-yl radical which is unsubstituted or disubstituted with a 4,4-dimethyl group or substituted at the 4-position with a spirocyclopentane group;

and/or one or two of the substituents $R_3$, $R_4$, $R_5$ represent(s) a halogen atom or a methyl or methoxy group; preferably $R_3$ is at the 4-position and represents a chlorine or bromine atom or a methoxy group, $R_4$, $R_5$ representing a hydrogen atom;

and/or one or two of the substituents $R_6$, $R_7$, $R_8$ represent(s) a halogen atom or a methyl group; preferably $R_6$ and $R_7$ are at the 2,4-position and represent two chlorine atoms, $R_8$ representing a hydrogen atom;

and their salts, their solvates and their hydrates.

According to the present invention, 5-(4-bromophenyl)-4-cyano-1-(2,4-dichlorophenyl)-N-tert-butyl-1H-pyrazole-3-carboxamide, 5-(4-bromophenyl)-4-cyano-1-(2,4-dichlorophenyl)-N-(1,1-dimethylpropyl)-1H-pyrazole-3-carboxamide, 5-(4-chlorophenyl)-4-cyano-1-(2,4-dichlorophenyl)-N-piperidin-1-yl-1H-pyrazole-3-carboxamide, 5-(4-methoxyphenyl)-4-cyano-1-1(2,4-dichlorophenyl)-N-tert-butyl-1H-pyrazole-3-carboxamide and 5-(4-chlorophenyl)-4-cyano-1-(2,4-dichlorophenyl)-N-hexahydrocyclopenta[c]pyrrol-2(1H)-yl-1H-pyrazole-3-carboxamide, are most particularly preferred.

The subject of the present invention is also a method for preparing the compounds according to the invention.

This method is characterized in that a functional derivative of 4-cyano-1,5-diphenylpyrazole-3-carboxylic acid of formula:

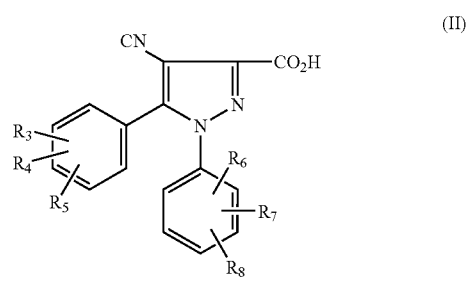

(II)

in which $R_3$, $R_4$, $R_5$, $R_6$, $R_7$, $R_8$ are as defined for (I), is treated with an amine of formula $HNR_1R_2$ (III) in which $R_1$ and $R_2$ are as defined for (I). Optionally, the compound thus obtained is converted to one of its salts or solvates.

As a functional derivative of the acid (II), it is possible to use the chloride of an acid, the anhydride, a mixed anhydride, a $C_1-C_4$ alkyl ester in which the alkyl is straight or branched, an activated ester, for example p-nitrophenyl ester, or the free acid opportunely activated, for example, with N,N-di-cyclohexylcarbodiimide or with benzotriazol-N-yloxo-tris(dimethylamino)phosphonium hexafluorophosphate (BOP) or benzotriazol-1-yloxotris(pyrrolidino)-phosphonium hexafluorophosphate (PyBOP).

Thus, in the method according to the invention, it is possible to react the chloride of a pyrazole-3-carboxylic acid, obtained by reacting thionyl chloride with the acid of formula (II), with an amine $HNR_1R_2$, in an inert solvent, such as a chlorinated solvent (dichloromethane, dichloroethane, chloroform for example), an ether (tetrahydrofuran, dioxane for example), or an amide (N,N-dimethylformamide for example) under an inert atmosphere, at a temperature of between 0° C. and room temperature, in the presence of a tertiary amine such as triethylamine, N-methyl-morpholine or pyridine.

An alternative method consists of preparing the mixed anhydride of the acid of formula (II) by reacting ethyl chloroformate with the acid of formula (II), in the presence of a base such as triethylamine, and in reacting it with an amine $HNR_1R_2$, in a solvent such as dichloromethane, under an inert atmosphere, at room temperature, in the presence of a base such as triethylamine.

The compounds of formula (II) may be prepared by various methods known in the literature, for example as described in J. Heterocyclic Chem., 1977, 14 (3), 375-381.

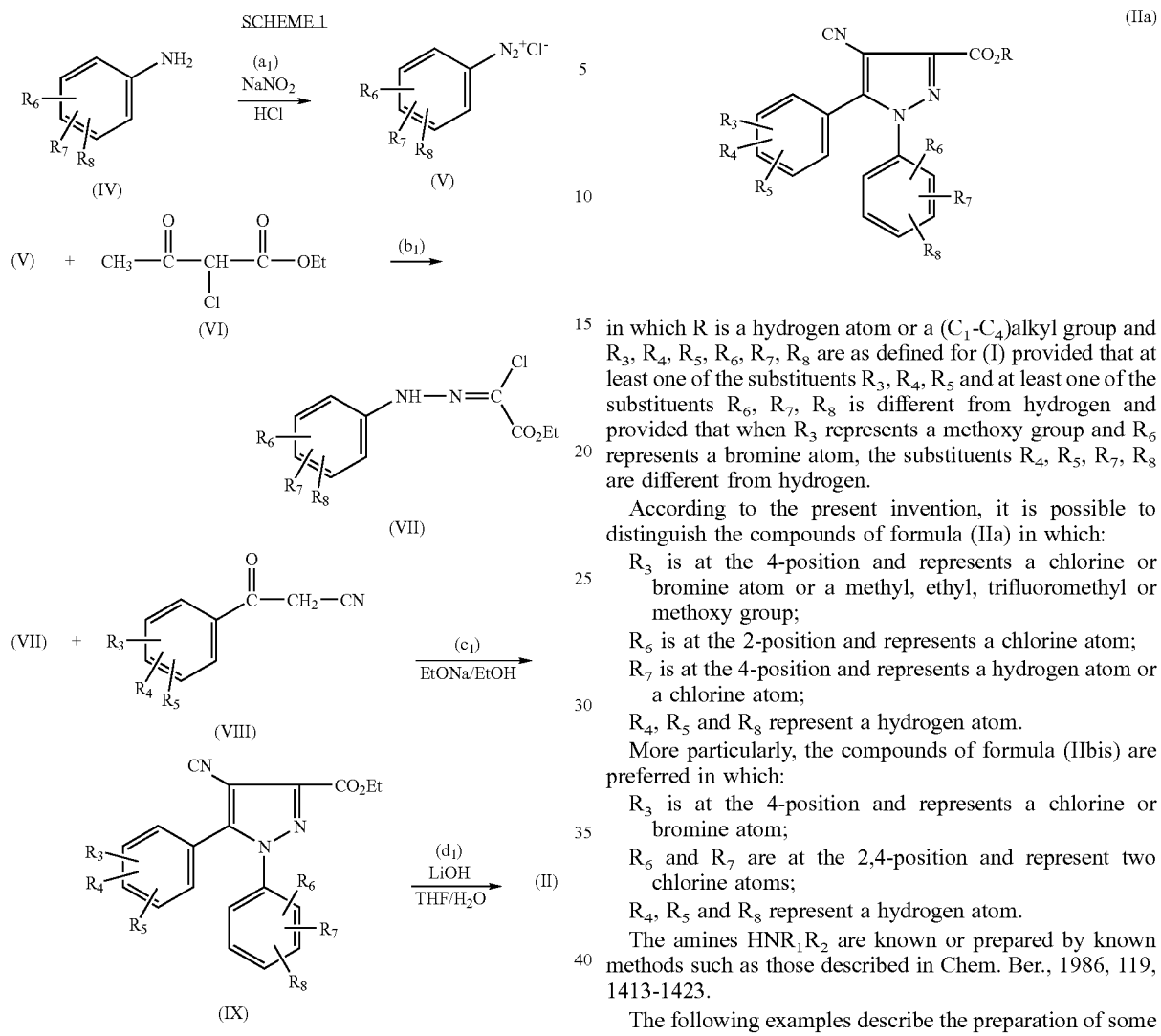

SCHEME 1

In step a₁) an aniline of formula (IV) is converted to a diazonium salt (V) by the action of a nitrite in an acidic medium, as described in Razdan et al., Med. Chem. Res., 1995, 5, 54. The diazonium salt (V) is then reacted with ethyl 2-chloro-3-oxo-butanoate (VI) to give the hydrazone derivative (VII).

The hydrazone derivative (VII) is fused with the nitrite of formula (VIII) in the presence of a strong base such as sodium ethoxide in ethanol in order to obtain the pyrazole derivative (IX). The latter is finally converted to an acid (II) by saponification using gentle conditions, for example LiOH in a THF/water mixture.

The acids of formula (II) and their esters of formula (IX) are generally novel. Some of these compounds are described in J. Heterocyclic Chem., 1977, 14 (3), 375-381; the ethyl ester of 1-(4-bromophenyl)-4-cyano-5(4-methoxyphenyl) 1H-pyrazole-3-carboxylic acid is cited in the Interchim. Intermediates catalog.

Thus, the subject of the present invention is also the compounds of formula:

in which R is a hydrogen atom or a $(C_1-C_4)$alkyl group and $R_3$, $R_4$, $R_5$, $R_6$, $R_7$, $R_8$ are as defined for (I) provided that at least one of the substituents $R_3$, $R_4$, $R_5$ and at least one of the substituents $R_6$, $R_7$, $R_8$ is different from hydrogen and provided that when $R_3$ represents a methoxy group and $R_6$ represents a bromine atom, the substituents $R_4$, $R_5$, $R_7$, $R_8$ are different from hydrogen.

According to the present invention, it is possible to distinguish the compounds of formula (IIa) in which:

$R_3$ is at the 4-position and represents a chlorine or bromine atom or a methyl, ethyl, trifluoromethyl or methoxy group;

$R_6$ is at the 2-position and represents a chlorine atom;

$R_7$ is at the 4-position and represents a hydrogen atom or a chlorine atom;

$R_4$, $R_5$ and $R_8$ represent a hydrogen atom.

More particularly, the compounds of formula (IIbis) are preferred in which:

$R_3$ is at the 4-position and represents a chlorine or bromine atom;

$R_6$ and $R_7$ are at the 2,4-position and represent two chlorine atoms;

$R_4$, $R_5$ and $R_8$ represent a hydrogen atom.

The amines $HNR_1R_2$ are known or prepared by known methods such as those described in Chem. Ber., 1986, 119, 1413-1423.

The following examples describe the preparation of some compounds in accordance with the invention. These examples are not limiting and merely illustrate the present invention. The exemplified compound numbers refer to those given in the table below, which illustrates the chemical structures and the physical properties of a few compounds according to the invention.

In the present description, the following abbreviations are used:

AcOEt: ethyl acetate; BOP: benzotriazolyloxytris-dimethylaminophosphonium hexafluorophosphate; DCM: Dichloromethane; DMF: dimethylformamide; EtOH: ethanol; m.p. melting point; iPr₂O: isopropyl ether; RT: room temperature; THF: tetrahydrofuran.

The compounds according to the invention are analyzed by LC/UV/MS (liquid chromatography/UV detection/mass spectrometry) coupling. The molecular peak (MH⁺) and the retention time (t) in minutes are measured.

There is used an Xterra Waters® MS C18 column, marketed by Waters, of 2.1×30 mm, 3.5 μm, at room temperature, flow rate 1 ml/minute.

The eluent is made up as follows:
solvent A: 0.025% of trifluoroacetic acid (TFA) in water
solvent B: 0.025% of TFA in acetonitrile.

Gradient: The percentage of solvent B varies from 0 to 100% over 2 minutes with a plateau at 100% of B for 1 minute.

The UV detection is carried out between 210 nm and 400 nm and the mass detection in chemical ionization mode at atmospheric pressure.

The NMR spectra were recorded at 200 MHz in DMSO-$d_6$.

For the interpretation of the nuclear magnetic resonance (NMR) spectra, the following abbreviations are used: s: singlet; d: doublet; m: unresolved complex; bs: broad singlet; dd: doublet of doublet; mt: multiplet.

Preparation 1
5-(4-Chlorophenyl)-4-cyano-1-(2,4-dichlorophenyl)-1H-pyrazole-3-carboxylic acid A) Ethyl chloro[(2,4-dichlorophenyl)hydrazino]acetate 7.3 g of dichloroaniline in 75 ml of a 24% HCl solution and 200 ml of water are mixed, with stirring, and the stirring is maintained for 2 hours. The mixture is cooled in an ice bath and a solution containing 3.1 g of $NaNO_2$ in 21 ml of water is added dropwise over 30 minutes. The mixture obtained is added to a solution containing 3.51 g of sodium acetate and 6.21 ml of ethyl 2-chloro-3-oxobutanoate in 450 ml of EtOH, cooled in an ice bath. The temperature is allowed to rise slowly while the stirring is maintained. The precipitate formed is filtered, washed with water and then dried under vacuum. 11.43 g of the expected compound are obtained.

NMR: 1.40 ppm: t: 3H; 4.40 ppm: d: 2H; 7.40-7.80 ppm: m: 3H; 9.25 ppm: s: 1H.

B) Ethyl 5-(4-chlorophenyl)-4-cyano-1-(2,4-dichlorophenyl)-1H-pyrazole-3-carboxylate A mixture containing 3.27 g of the compound from the preceding step, 1.99 g of 3-(4-chlorophenyl)-3-oxopropanenitrile in 120 ml of EtOH and sodium ethoxide prepared by mixing 0.28 g of sodium in 25 ml of EtOH, are heated under reflux for 18 hours. After returning to RT, the mixture is evaporated to dryness and taken up in 150 ml of AcOEt, the precipitate formed is filtered and the organic phase is washed with water and then with a saturated NaCl solution. The oil obtained is chromatographed on silica, eluting with an AcOEt/toluene (2/98 to 3/97; v/v) mixture. The solid obtained is recrystallized twice from a $CH_2Cl_2/iPr_2O$ mixture to give 1.12 g of the expected compound in the form of white crystals, m.p.=112° C.

C) 5-(4-Chlorophenyl)-4-cyano-1-(2,4-dichlorophenyl)-1H-pyrazole-3-carboxylic acid 0.436 g of the ester obtained in the preceding step in 25 ml of THF and 50 mg of LiOH in 5 ml of water are mixed and the mixture is heated for 2 hours at 65° C. The medium is concentrated by half, the reaction medium is poured into 50 ml of ice-cold water and 5 ml of 5% HCl. The organic mixture is extracted with $CH_2Cl_2$ and then washed with NaCl. 0.41 g of the expected compound is obtained in solid form. m.p.=132-137° C.

NMR: 7.42 ppm: d: 2H; 7.61 ppm: d: 2H; 7.69 ppm: dd: 1H; 7.89 ppm: s: 1H; 7.92 ppm: d: 1H; 13.8-14.6 ppm: bs: 1H.

Preparation 2
5-(4-Bromophenyl)-4-cyano-1-(2,4-dichlorophenyl)-1H-pyrazole-3-carboxylic acid A) 3-(4-Bromophenyl)-3-oxopropanenitrile A solution containing 9.4 g of KCN in 20 ml of water is prepared and then it is poured dropwise over a mixture containing 20 g of 2-bromo-1-(4-bromophenyl)ethanone dissolved in 800 ml of 90% ethanol. After stirring for 5 hours at RT, the solid formed is filtered and then it is rinsed with ice-cold water. The solid obtained is dissolved in 400 ml of water and then activated charcoal is added, the mixture is kept stirring for 20 minutes, and then filtered on Celite®. The filtrate obtained is treated with HCl at 10% and the white precipitate formed is filtered, washed with water and then dried under vacuum. 7.63 g of the expected compound are obtained. m.p.=164° C.

NMR: 4.75 ppm: bs: 2H; 7.80 ppm: mt: 4H

B) Ethyl 5-(4-bromophenyl)-4-cyano-1-(2,4-dichlorophenyl)-1H-pyrazole-3-carboxylate A sodium ethoxide solution is prepared by mixing 0.86 g of sodium in 107 ml of EtOH, 7.63 g of the compound prepared in the preceding step in 610 ml of EtOH are rapidly added, followed by 9.2 g of the compound obtained in step A of Preparation 1 and the reaction medium is kept stirring overnight at RT. The insoluble material is filtered and then the filtrate is concentrated under vacuum. The product obtained is concentrated on silica, eluting with a toluene/AcOEt (96/4; v/v) mixture. 5 g of the expected compound are obtained.

NMR: 1.25 ppm: t: 3H; 4.30 ppm: q: 2H; 7.20 ppm: d: 2H; 7.50-7.70 ppm: m: 3H; 7.70-8.00 ppm: m: 2H.

C) 5-(4-Bromophenyl)-4-cyano-1-(2,4-dichlorophenyl)-1H-pyrazole-3-carboxylic acid 2.8 g of the ester obtained in the preceding step are placed in 90 ml of THF and 0.4 g of LiOH in 8 ml of water are added and then the mixture is heated at 65° C. for 3 hours. The reaction medium is poured over a mixture of 240 ml of ice-cold water and 16 ml of HCl at 10%. The organic phase is extracted with $CH_2Cl_2$ and then washed with a saturated NaCl solution. 2.3 g of the expected compound are obtained.

NMR: 7.30 ppm: d: 2H; 7.60-7.80 ppm: m: 3H; 7.80-8.00 ppm: m: 2H; 14.15 ppm: bs: 1H.

By carrying out the procedure according to the procedures set forth in the above preparations, the compounds in the following table are obtained:

TABLE 1

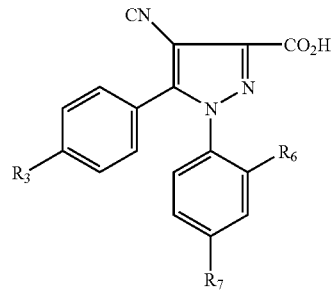

(II)

| Preparation | $R_3$ | $R_6$, $R_7$ | Melting point |
|---|---|---|---|
| 3 | —OMe | —Cl, —Cl | m.p. = 230° C. |
| 4 | —Me | —Cl, —Cl | m.p. = 223° C. |
| 5 | —$CF_3$ | —Cl, —Cl | m.p. = 238° C. |
| 6 | —Et | —Cl, H | m.p. = 254° C. |

EXAMPLE 1

Compound 1

5-(4-Chlorophenyl)-4-cyano-1-(2,4-dichlorophenyl)-N-piperidin-1-yl-1H-pyrazole-3-carboxamide 0.39 g of the acid from Preparation 1 is added dropwise to a solution containing 0.20 ml of 1-aminopiperidine and 0.50 ml of triethylamine in 15 ml of $CH_2Cl_2$, and then 0.80 g of BOP is added dropwise and the mixture is kept stirring at RT for 20 hours. The reaction medium is hydrolyzed with water and then the organic phase is washed with a 2% HCl solution, with a 5% $Na_2CO_3$ solution and then with a saturated NaCl solution. After drying, the product obtained is chromatographed on silica, eluting with an $MeOH/CH_2Cl_2$ (0.5/99.5; v/v) mixture to give a foam. The expected compound crystallizes from a $CH_2Cl_2/iPr_2O$ mixture, 0.28 g is obtained, m.p.=227-229° C.

EXAMPLE 2

Compound 12

5-(4-Bromophenyl)-4-cyano-1-(2,4-dichlorophenyl)-N-tert-butyl-1H-pyrazole-3-carboxamide 0.437 g of the acid from Preparation 2, 0.19 ml of tert-butylamine, 0.5 ml of $NEt_3$ and then 0.79 g of BOP are mixed in 20 ml of $CH_2Cl_2$ and the mixture is kept stirring at RT for 48 hours. The reaction medium is hydrolyzed with water and then the organic phase is washed with a 2% HCl solution, a 5% $Na_2CO_3$ solution and then a saturated NaCl solution. After drying, the product obtained is chromatographed on silica, eluting with a toluene/AcOEt (95/5; v/v) mixture to give a product which crystallizes from isopropyl ether. 370 mg are obtained, m.p.=184° C.

NMR: 1.35 ppm; s: 9H; 7.30 ppm: d: 2H; 7.60-8.00 ppm; m: 6H.

The table which follows illustrates the chemical structure and the physical properties of a few examples of compounds according to the invention.

In this table, Me, Et and tBu represent the methyl, ethyl and tert-butyl groups, respectively.

TABLE 2

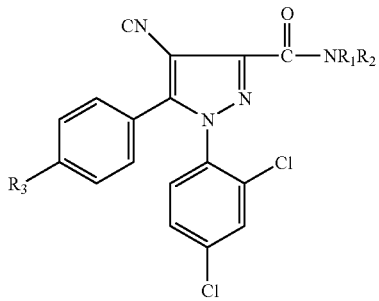

(I)

| Compounds | $R_3$ | $R_6$, $R_7$ | —$NR_1R_2$ | characterization |
|---|---|---|---|---|
| 1 | —Cl | —Cl, —Cl | —NH—N(piperidine) | m.p. = 227° C. |
| 2 | —Br | —Cl, —Cl | —NH—N(piperidine) | m.p. = 228° C. |
| 3 | —Cl | —Cl, —Cl | —NH-tBu | m.p. = 197° C. |
| 4 | —Cl | —Cl, —Cl | —NH—C(Me)(Me)—Et | m.p. = 159° C. |
| 5 | —Cl | —Cl, —Cl | —NH—N(spiro) | m.p. = 243° C. |
| 6 | —Cl | —Cl, —Cl | —NH—N(4,4-dimethylpiperidine) | m.p. = 233° C. |

TABLE 2-continued

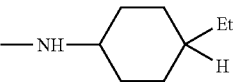

(I)

| Compounds | R₃ | R₆, R₇ | —NR₁R₂ | characterization |
|---|---|---|---|---|
| 7 | —Cl | —Cl, —Cl | —NH-(4-ethylcyclohexyl, Et up, H down) | m.p. = 200° C. +polar |
| 8 | —Cl | —Cl, —Cl | —NH-(4-ethylcyclohexyl, H up, Et down) | m.p. = 241° C. −polar |
| 9 | —Br | —Cl, —Cl | —NH—N(4,4-dimethylpiperidine) | m.p. = 231° C. |
| 10 | —Br | —Cl, —Cl | —NH—N(2-azaspiro[4.5] or 8-azaspiro[4.5]decane) | m.p. = 252° C. |
| 11 | —Br | —Cl, —Cl | —NH—C(Me)(Me)Et | m.p. = 160° C. |
| 12 | —Br | —Cl, —Cl | —NH-tBu | m.p. = 184° C. |
| 13 | —Br | —Cl, —Cl | —NH-(4-ethylcyclohexyl, Et up, H down) | m.p. = 212° C. +polar |
| 14 | —Br | —Cl, —Cl | —NH-(4-ethylcyclohexyl, H up, Et down) | m.p. = 250° C. −polar |
| 15 | —Cl | —Cl, —Cl | —N(1-methyl-4-phenyl-4-acetylpiperidine) | MH⁺ = 577 t = 2.59 |
| 16 | —Cl | —Cl, —Cl | —NH-(trimethylcyclohexyl stereochemistry) | MH⁺ = 527 t = 2.78 |
| 17 | —Cl | —Cl, —Cl | —NH-(4-methoxyphenyl) | MH⁺ = 497 t = 2.52 |

TABLE 2-continued

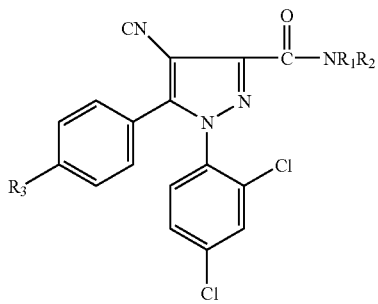

(I)

| Compounds | R₃ | R₆, R₇ | —NR₁R₂ | characterization |
|---|---|---|---|---|
| 18 | —Cl | —Cl, —Cl | —NH—C₆H₄—F (4-F) | MH⁺ = 485<br>t = 2.55 |
| 19 | —Cl | —Cl, —Cl | —NH—CH(Me)—CH(Ph)(4-Cl-C₆H₄) | MH⁺ = 619<br>t = 2.71 |
| 20 | —Cl | —Cl, —Cl | —NH-(bicyclic) | MH⁺ = 499<br>t = 2.80 |
| 21 | —Br | —Cl, —Cl | —NH—C₆H₈(4,4-diMe) | m.p. = 209° C. |
| 22 | —OMe | —Cl, H | —NH—N(piperidine) | m.p. = 260° C. |
| 23 | —OMe | —Cl, —Cl | —NH-tBu | m.p. = 229° C. |
| 24 | —Et | —Cl, H | —NH—N(piperidine) | m.p. = 227° C. |
| 25 | —Et | —Cl, —Cl | —NH-tBu | m.p. = 225° C. |
| 26 | —Et | —Cl, H | —NH—C(Me)₂Et | m.p. = 192° C. |
| 27 | —Br | —Cl, —Cl | —NH—C₆H₁₀—OH (trans) | m.p. = 222° C. |
| 28 | —CF₃ | —Cl, —Cl | —NH-tBu | m.p. = 192° C. |
| 29 | —CF₃ | —Cl, —Cl | —NH—N(piperidine) | m.p. = 223° C. |

TABLE 2-continued
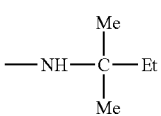
(I)
| Compounds | R₃ | R₆, R₇ | —NR₁R₂ | characterization |
|---|---|---|---|---|
| 30 | —CF₃ | —Cl, —Cl | —NH—C(Me)(Et)Me | m.p. = 177° C. |
| 31 | —OMe | —Cl, —Cl | —NH-tBu | m.p. = 157° C. |
| 32 | —OMe | —Cl, —Cl | —NH—N(piperidine) | m.p. = 180° C. |
| 33 | —OMe | —Cl, —Cl | —NH—C(Me)(Et)Me | m.p. = 143° C. |
| 34 | —Me | —Cl, —Cl | —NH-tBu | m.p. = 171° C. |
| 35 | —Cl | —Cl, —Cl | 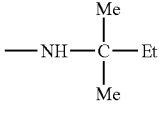 | m.p. = 239° C. |
| 36 | —Me | —Cl, —Cl | —NH—C(Me)(Et)Me | m.p. = 157° C. |
| 37 | —Me | —Cl, —Cl | —NH—N(piperidine) | m.p. = 206° C. |
| 38 | —OMe | —Cl, —Cl | 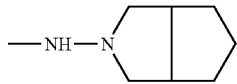 | m.p. = 197° C. |
| 39 | —OMe | —Cl, —Cl | 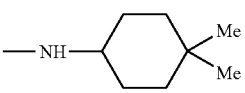 | m.p. = 206° C. |
| 40 | —OMe | —Cl, —Cl | 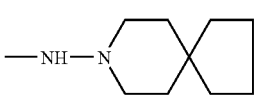 | m.p. = 266° C. |
| 41 | —OMe | —Cl, —Cl | 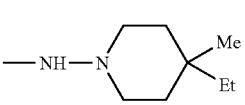 | m.p. = 196° C. |

TABLE 2-continued (I)

| Compounds | R$_3$ | R$_6$, R$_7$ | —NR$_1$R$_2$ | characterization |
|---|---|---|---|---|
| 42 | —OMe | —Cl, —Cl | (piperidine with phenyl and C(O)Me substituents) | m.p. = 164° C. |

The compounds according to the invention have been the subject of pharmacological trials which make it possible to determine their antagonist effect of CB$_1$, cannabinoid receptors.

The compounds of formula (I) possess a very good affinity in vitro (IC$_{50}$≦10$^{-7}$M) for the CB$_1$ cannabinoid receptors, under the experimental conditions described by M. Rinaldi-Carmona et al. (FEBS 1994, 350, 240-244).

The antagonist nature of the compounds of formula (I) has been demonstrated by the results obtained in adenylate cyclase inhibition models as in M. Rinaldi-Carmona et al., J. Pharmacol. Exp. Ther., 1996, 278, 871-878 and M. Bouaboula et al., J. Biol. Chem., 1997, 272, 22330-22339.

The compounds according to the invention were tested in vivo (binding ex vivo) in mice after intravenous and/or oral administration, according to the experimental conditions described by Rinaldi-Carmona et al. (J. Pharmacol. Exp., 1998, 284, 644-650). By the intravenous route, the effective dose (ED$_{50}$) of these compounds for the CB$_1$ receptors is less than or equal to 10 mg/kg. By the oral route, compounds 2, 3, 4, 11 and 12 have an ED$_{50}$ of between 1 and 20 mg/kg for the CB$_1$ receptors.

The toxicity of the compounds of formula (I) is compatible with their use as a medicament.

According to another of these aspects, the present invention relates to the use of a compound of formula (I), or of one of its pharmaceutically acceptable salts, solvates or hydrates, for the preparation of medicaments intended for treating or preventing diseases involving the CB$_1$ cannabinoid receptors.

For example and without limitation, the compounds of formula (I) are useful as psychotropic medicaments, in particular for the treatment of psychiatric disorders including anxiety, depression, mood disorders, insomnia, delirium disorders, obsessive disorders, psychoses in general, schizophrenia, attention deficit hyperactivity disorder (ADHD), in particular in hyperkinetic children (MBD), and for the treatment of disorders linked to the use of psychotropic substances, in particular in the case of a substance abuse and/or of dependence on a substance, including alcohol dependence and nicotine dependence.

The compounds of formula (I) according to the invention may be used as medicaments for the treatment of migraine, stress, diseases of psychosomatic origin, panic attacks, epileptic attacks, motion disorders, in particular dyskinesia or Parkinson's disease, tremors and dystonia.

The compounds of formula (I) according to the invention can also be used as medicaments in the treatment of memory disorders, cognitive disorders, in particular in the treatment of senile dementia, Alzheimer's disease, and in the treatment of attention or vigilance disorders. Furthermore, the compounds of formula (I) may also be useful as neuroprotectants, in the treatment of ischemia, cranial traumas and the treatment of neurodegenerative diseases: including chorea, Huntington's chorea, Tourette's syndrome.

The compounds of formula (I) according to the invention can be used as medicaments in the treatment of pain: neuropathic pain, acute peripheral pain, chronic pain of inflammatory origin.

The compounds of formula (I) according to the invention may be used as medicaments in the treatment of appetite disorders, craving disorders (for sugars, carbohydrates, drugs, alcohol or any appetizing substance) and/or alimentary canal disorders, in particular as anorexics or for the treatment of obesity or of bulimia and for the treatment of type II diabetes or non-insulin-dependent diabetes and for the treatment of dyslipidemia and of metabolic syndrome. Furthermore, the compounds of formula (I) according to the invention may be used as medicaments in the treatment of gastrointestinal disorders, diarrheal disorders, ulcers, emesis, bladder and urinary disorders, disorders of endocrine origin, cardiovascular disorders, hypotension, hemorrhagic shock, septic shock, chronic cirrhosis of the liver, asthma, chronic bronchitis and chronic obstructive pulmonary disease, Raynaud's syndrome, glaucoma, fertility disorders, inflammatory phenomena, immune system diseases, in particular autoimmune and neuroinflammatory diseases such as rheumatoid arthritis, reactive arthritis, diseases causing demyelinization, multiple sclerosis, infectious and viral diseases such as encephalitis, stroke and as medicaments for anticancer chemotherapy and for the treatment of Guillain-Barré syndrome.

According to the present invention, the compounds of formula (I) are particularly useful for the treatment of psychotic disorders, in particular schizophrenia, attention deficit hyperactivity disorders (ADHD), in particular in hyperkinetic children (MBD); for the treatment of appetite disorders and obesity, for the treatment of memory and cognitive disorders; for the treatment of alcohol dependence, nicotine dependence, that is to say for withdrawal from alcohol and for smoking cessation; and for the treatment of dyslipidemia and of metabolic syndrome.

According to one of its aspects, the present invention relates to the use of a compound of formula (I), of its pharmaceutically acceptable salts and of their solvates or hydrates, for the treatment of the disorders and diseases indicated above.

The compounds of formula (I) according to the invention may be used in combination with one or more other active ingredients useful for the prevention and/or treatment of the diseases indicated above: by way of example of active ingredients which may be combined with a compound of formula (I), there may be mentioned antipsychotics, anxiolytics, memory enhancers, anti-Parkinson agents, antiepileptics, anorexics or other antiobesity agents, nicotine agonists, monoamine oxidase inhibitors, analgesics, antiinflammatory agents, antihypertensives such as: angiotensin II $AT_1$ receptor antagonists, converting enzyme inhibitors, calcium antagonists, beta-blockers, antidiabetics, antihyperlipidemics, anticholesterolemics, PPAR (peroxisome proliferator activated receptor) agonists.

The compound according to the invention is generally administered in dosage unit form.

Said dosage units are preferably formulated in pharmaceutical compositions in which the active ingredient is mixed with a pharmaceutical excipient.

Thus according to another of its aspects, the present invention relates to pharmaceutical compositions containing, as active ingredient, a compound of formula (I), one of its pharmaceutically acceptable salts or one of their solvates.

The compound of formula (I) above and its pharmaceutically acceptable salts or solvates may be used in daily doses of 0.01 to 100 mg per kg of body weight of the mammal to be treated, preferably in daily doses of 0.02 to 50 mg/kg. In human beings, the dose can vary preferably from 0.05 to 4000 mg per day, more particularly from 0.1 to 1000 mg per day according to the age of the subject to be treated or the type of treatment, namely prophylactic or curative. Although these dosages are examples of average situations, there may be particular cases when higher or lower dosages are appropriate, such dosages also belong to the invention. According to customary practice, the dosage appropriate for each patient is determined by the doctor according to the mode of administration, the age, the weight and the response of said patient.

In the pharmaceutical compositions of the present invention for oral, sublingual, inhaled, subcutaneous, intramuscular, intravenous, transdermal, local or rectal administration, the active ingredient may be administered in unit form for administration, mixed with conventional pharmaceutical carriers, to animals and to humans. The appropriate unit forms for administration comprise the forms by the oral route such as tablets, gelatin capsules, powders, granules and oral solutions or suspensions, the forms for sublingual or buccal administration, aerosols, the forms for topical administration, implants, the forms for subcutaneous, intramuscular, intravenous, intranasal or intraocular administration and the forms for rectal administration.

In the pharmaceutical compositions of the present invention, the active ingredient is generally formulated in dosage units containing from 0.05 to 1000 mg, advantageously from 0.1 to 500 mg, preferably from 1 to 200 mg of said active ingredient per dosage unit for daily administrations.

By way of example, a unit form for administration of a compound according to the invention in tablet form may comprise the following compounds:

| | |
|---|---|
| Compound according to the invention | 50.0 mg |
| Mannitol | 223.75 mg |
| Croscaramellose sodium | 6.0 mg |
| Maize starch | 15.0 mg |
| Hydroxypropylmethylcellulose | 2.25 mg |
| Magnesium stearate | 3.0 mg |

By the oral route, the dose of active ingredient administered per day may be up to 0.01 to 100 mg/kg, in single or divided doses, preferably 0.02 to 50 mg/kg.

There may be specific cases where higher or lower doses are appropriate; such doses do not depart from the scope of the invention. According to the usual practice, the appropriate dose for each patient is determined by the doctor according to the mode of administration, the weight and the response of said patient.

The present invention, according to another of its aspects, also relates to a method for treating the pathologies indicated above, which comprises the administration, to a patient, of an effective dose of a compound according to the invention, or one of its pharmaceutically acceptable salts or hydrates or solvates.

What is claimed is:

1. A compound of formula (I):

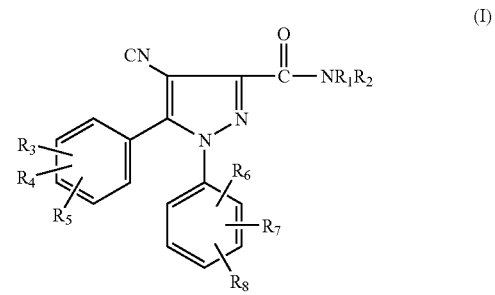

in which:

$R_1$ represents hydrogen or a $(C_1-C_4)$alkyl;

$R_2$ represents:

an $NR_9R_{10}$ group;

$R_3, R_4, R_5, R_6, R_7, R_8$ represent, each independently of the other, a hydrogen, halogen, a $(C_1-C_6)$alkyl, $(C_1-C_6)$ alkoxy or trifluoromethyl; provided that at least one of the substituents $R_3, R_4, R_5, R_6, R_7, R_8$ is different from hydrogen;

$R_9$ represents a hydrogen atom;

$R_{10}$ represents a $(C_3-C_6)$alkyl;

or $R_9$ and $R_{10}$ together with the nitrogen atom to which they are attached constitute a saturated or unsaturated heterocyclic radical of 5 to 10 atoms, optionally containing a second heteroatom chosen from O or N, said radical being unsubstituted or substituted once or several times with a $(C_1-C_4)$alkyl, hydroxyl, $(C_1-C_4)$ alkoxy, methoxy$(C_1-C_2)$alkylene, $(C_1-C_4)$alkanoyl group or substituted with a spirocyclobutane, a spirocyclopentane or a spirocyclohexane; or
a pharmaceutically acceptable salt thereof or a hydrate or a solvate thereof.

2. The compound of formula (I), as set forth in claim 1, wherein:
$R_1$ represents hydrogen or a $(C_1-C_4)$alkyl;
$R_2$ represents an $NR_9R_{10}$ group in which $R_9$ and $R_{10}$ together with the nitrogen atom to which they are attached constitute a piperidin-1-yl radical which is unsubstituted or disubstituted with a 4,4-dimethyl group or substituted at the 4-position with a spirocyclopentane group;
at least one of the substituents $R_3$, $R_4$ or $R_5$ represents a halogen atom, a methyl or methoxy; and
at least one of the substituents $R_6$, $R_7$ or $R_8$ represents a halogen atom or a methyl; or
a pharmaceutically acceptable salt thereof or a hydrate or a solvate thereof.

3. The compound of formula (I), as set forth in claim 1, wherein:
$R_1$ represents hydrogen;
$R_2$ represents an $NR_9R_{10}$ group in which $R_9$ and $R_{10}$ together with the nitrogen atom to which they are attached constitute a piperidin-1-yl radical which is unsubstituted or disubstituted with a 4,4-dimethyl group or substituted at the 4-position with a spirocyclopentane group;
$R_3$ is at the 4-position and represents chlorine, bromine or methoxy;
$R_4$ and $R_5$ are hydrogen;
$R_6$ and $R_7$ are at the 2,4-position and represent 2 chlorine atoms; and
$R_8$ is hydrogen; or
a pharmaceutically acceptable salt thereof or a hydrate or a solvate thereof.

4. The compound, as set forth in claim 1, chosen from:
5-(4-chlorophenyl)-4-cyano-1-(2,4-dichlorophenyl)-N-piperidin-1-yl-1H-pyrazole-3-carboxamide and
5-(4-bromophenyl)-4-cyano-1-(2,4-dichlorophenyl)-N-piperidin-1-yl-1H-pyrazole-3-carboxamide; or
a pharmaceutically acceptable salt thereof or a hydrate or a solvate thereof.

5. A method for preparing a compound of formula (I) as set forth in claim 1, comprising reacting 4-cyano-1,5-diphenylpyrazole-3-carboxylic acid of formula II or a functional derivative thereof:

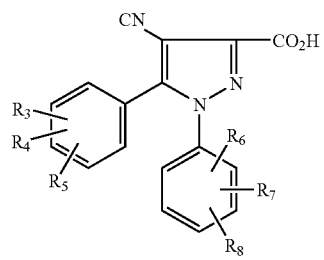

(II)

in which $R_3$, $R_4$, $R_5$, $R_6$, $R_7$, $R_8$ are as defined in claim 1, with an amine of formula $HNR_1R_2$ (III) in which $R_1$ and $R_2$ are as defined in claim 1.

6. A pharmaceutical composition comprising a compound of formula (I) or a pharmaceutically acceptable salt, a hydrate or a solvate thereof, in combination with at least one pharmaceutically acceptable excipient:

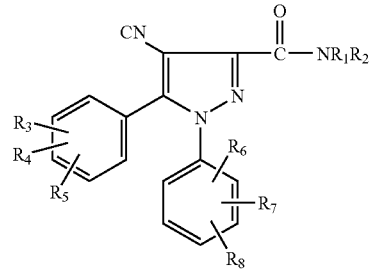

(I)

in which:
$R_1$ represents hydrogen or a $(C_1-C_4)$alkyl;
$R_2$ represents:
an $NR_9R_{10}$ group;
$R_3$, $R_4$, $R_5$, $R_6$, $R_7$, $R_8$ represent, each independently of the other, a hydrogen, halogen, a $(C_1-C_6)$alkyl, $(C_1-C_6)$ alkoxy or trifluoromethyl; provided that at least one of the substituents $R_3$, $R_4$, $R_5$, $R_6$, $R_7$, $R_8$ is different from hydrogen;
$R_9$ represents a hydrogen atom;
$R_{10}$ represents a $(C_3-C_6)$alkyl;
or $R_9$ and $R_{10}$ together with the nitrogen atom to which they are attached constitute a saturated or unsaturated heterocyclic radical of 5 to 10 atoms, optionally containing a second heteroatom chosen from O or N, said radical being unsubstituted or substituted once or several times with a $(C_1-C_4)$alkyl, hydroxyl, $(C_1-C_4)$ alkoxy, methoxy$(C_1-C_2)$alkylene, $(C_1-C_4)$alkanoyl group or substituted with a spirocyclobutane, a spirocyclopentane or a spirocyclohexane.

7. The composition as set forth in claim 6 wherein:
$R_1$ represents hydrogen or a $(C_1-C_4)$alkyl;
$R_2$ represents an $NR_9R_{10}$ group in which $R_9$ and $R_{10}$ together with the nitrogen atom to which they are attached constitute a piperidin-1-yl radical which is unsubstituted or disubstituted with a 4,4-dimethyl group or substituted at the 4-position with a spirocyclopentane group;
at least one of the substituents $R_3$, $R_4$ or $R_5$ represents a halogen atom, a methyl or methoxy; and
at least one of the substituents $R_6$, $R_7$ or $R_8$ represents a halogen atom or a methyl.

8. The composition as set forth in claim 6, wherein:
$R_1$ represents hydrogen;
$R_2$ represents an $NR_9R_{10}$ group in which $R_9$ and $R_{10}$ together with the nitrogen atom to which they are attached constitute a piperidin-1-yl radical which is unsubstituted or disubstituted with a 4,4-dimethyl group or substituted at the 4-position with a spirocyclopentane group;
$R_3$ is at the 4-position and represents chlorine, bromine or methoxy;
$R_4$ and $R_5$ are hydrogen;

$R_6$ and $R_7$ are at the 2,4-position and represent 2 chlorine atoms; and $R_8$ is hydrogen.

9. The composition as set forth in claim 6, wherein said compound is chosen from:

5-(4-chlorophenyl)-4-cyano-1-(2,4-dichlorophenyl)-N-piperidin-1-yl-1H-pyrazole-3-carboxamide and 5-(4-bromophenyl)-4-cyano-1-(2,4-dichlorophenyl)-N-piperidin-1-yl-1H-pyrazole-3-carboxamide; or a pharmaceutically acceptable salt thereof or a hydrate or a solvate thereof.

* * * * *